(12) United States Patent
Barr et al.

(10) Patent No.: US 10,996,047 B2
(45) Date of Patent: May 4, 2021

(54) MEASURING APPARTUS

(71) Applicant: Capaltec Limited, Hillsborough (GB)

(72) Inventors: Andrew Barr, Anahilt (GB); Michael Grace, Nenagh (IE)

(73) Assignee: Capaltec Limited, Hillsborough (GB)

( * ) Notice: Subject to any disclaimer, the term of this patent is extended or adjusted under 35 U.S.C. 154(b) by 943 days.

(21) Appl. No.: 15/510,262

(22) PCT Filed: Sep. 9, 2015

(86) PCT No.: PCT/GB2015/052602
§ 371 (c)(1),
(2) Date: Mar. 10, 2017

(87) PCT Pub. No.: WO2016/038361
PCT Pub. Date: Mar. 17, 2016

(65) Prior Publication Data
US 2017/0241770 A1    Aug. 24, 2017

Related U.S. Application Data

(63) Continuation of application No. 14/618,428, filed on Feb. 10, 2015, now abandoned.

(30) Foreign Application Priority Data

Sep. 10, 2014    (GB) .................................... 1416023

(51) Int. Cl.
*G01C 3/08*    (2006.01)
*G01B 11/06*    (2006.01)
(Continued)

(52) U.S. Cl.
CPC .......... *G01B 11/0608* (2013.01); *A01K 29/00* (2013.01); *A61B 5/1071* (2013.01);
(Continued)

(58) Field of Classification Search
CPC ..... G01B 11/0608; G01B 11/02; G01S 17/86; G01S 7/4808; G01S 7/4813; G01S 17/36;
(Continued)

(56) References Cited

U.S. PATENT DOCUMENTS

2005/0155246 A1    7/2005 Montagnino
2006/0002233 A1    1/2006 Malard
(Continued)

FOREIGN PATENT DOCUMENTS

CN    201628771 U    1/2010
CN    102506719 A    6/2012
(Continued)

OTHER PUBLICATIONS

Search Report (GB1416023.8), dated Jul. 30, 2015.
(Continued)

*Primary Examiner* — Samantha K Abraham
(74) *Attorney, Agent, or Firm* — Gregory L. Porter; Hunton Andrews Kurth LLP

(57) ABSTRACT

A height measuring apparatus comprising a main body portion adapted for placement upon an object to be measured, and a movable portion which is movable relative to the main body portion, wherein the movable portion comprises a laser source and a photo detector, the movable portion being movable so that a laser beam from the laser source can be directed to the ground when the main body is placed on the object to be measured.

12 Claims, 6 Drawing Sheets

(51) Int. Cl.
  *A61B 5/107* (2006.01)
  *G01S 7/48* (2006.01)
  *G01S 7/481* (2006.01)
  *G01S 17/36* (2006.01)
  *G01B 11/02* (2006.01)
  *G01C 5/00* (2006.01)
  *G01S 17/42* (2006.01)
  *G01S 17/86* (2020.01)
  *A01K 29/00* (2006.01)
  *G01P 15/18* (2013.01)
  *A61B 5/00* (2006.01)
  *G01C 3/00* (2006.01)
  *G12B 5/00* (2006.01)

(52) U.S. Cl.
  CPC .......... *A61B 5/1072* (2013.01); *A61B 5/1079* (2013.01); *G01B 11/02* (2013.01); *G01C 5/00* (2013.01); *G01P 15/18* (2013.01); *G01S 7/4808* (2013.01); *G01S 7/4813* (2013.01); *G01S 17/36* (2013.01); *G01S 17/42* (2013.01); *G01S 17/86* (2020.01); *A61B 5/6814* (2013.01); *A61B 2560/0406* (2013.01); *A61B 2562/0219* (2013.01); *G01C 3/00* (2013.01); *G12B 5/00* (2013.01)

(58) Field of Classification Search
  CPC ....... G01S 17/42; A01K 29/00; A61B 5/1071; A61B 5/1072; A61B 5/1079; A61B 5/6814; A61B 2560/0406; A61B 2562/0219; G01P 15/18; G01C 3/00; G01C 5/00; G12B 5/00
  See application file for complete search history.

(56) References Cited

U.S. PATENT DOCUMENTS

2010/0298708 A1 11/2010 Pan
2014/0351073 A1\* 11/2014 Murphy ................ G01B 11/02
  705/23

FOREIGN PATENT DOCUMENTS

| DE | 202014007032 U | 9/2014 |
| DE | 202014007032 U1 | 9/2014 |
| GB | 2481199 A | 12/2011 |
| GB | 2519627 A | 4/2015 |
| KR | 100929237 A | 12/2012 |
| KR | 20120131132 A | 12/2012 |
| KR | 1020120131132 A | 5/2014 |
| WO | 2003062744 A1 | 7/2003 |

OTHER PUBLICATIONS

PCT Search Report & Written Opinion (PCT/GB2015/052602), dated Dec. 16, 2015.
Chinese Office Action (CN 201580056365.9), dated Aug. 2, 2019.
English Summary of Chinese Office Action (CN 201580056365.9), dated Aug. 22, 2019.
Examination Report (GB 1416023.8), dated Feb. 20, 2020.

\* cited by examiner

MEASURING APPARTUS

FIELD OF THE INVENTION

The present invention relates to an apparatus for measuring the heights of subjects, in particular where the apparatus is placed on top of the subject to be measured.

BACKGROUND OF THE INVENTION

There exist many instances where there is a requirement to accurately measure the height of an object or subject. For example, during medical examinations the height of a patient is often recorded. Similarly, the height of a horse is an important metric for classification purposes. Height is also a critical parameter in the management of cattle, since it dictates the 'Frame Score', which is used to dictate breeding and nutrition programmes. Such measurements are usually taken using measuring tapes or sticks. These are considered direct measurements. A measuring stick generally comprises an upright wooden ruler marked out in suitable units, and has horizontal sliding arm or 'cross-bar' that is arranged perpendicularly to the ruler. The subject to be measured is then stood upright alongside the ruler and the horizontal arm is lowered until it contacts the point on the subject where the height measurement is to be taken from. With a human, this point would be the top of the head; with a horse this would be at the withers; and with a cow at the top of its hip bone. The corresponding reading on the ruler at this point provides the height measurement.

Measuring sticks as described above present a number of drawbacks. Firstly there is an inherent potential for error in the measurement made. This is because the measurement is taken on the vertical ruler and not at the horizontal point of contact with the subject. In other words, the point of measurement is displaced. Consequently, if the sliding arm is not perfectly perpendicular to the ruler, an error is introduced into the measurement. Similarly, error may be introduced by poor calibration or due to the judgement of the user. Furthermore, the use of measuring sticks involves significant noise. In the case of animals, this can cause distress and unwanted movement, leading to flawed readings. Still furthermore, measuring sticks are by their nature, large and lack portability and so their practical use is often restricted to a fixed location. When transported, the size and construction of measuring sticks makes then susceptible to damage, and wear which causes the calibration of such devices to be eroded over time, leading to further inaccuracies. Tapes are also prey to mistakes, particularly when used for vertical measurement. This is mainly because they are not made of rigid material and can bend. In addition, in order to record a measurement, users have to look at both the point of contact for measurement whilst ensuring the base of the tape remains on the floor. Combining these tasks introduces huge scope for human error.

Alternative means of height measurement, such as rangefinders, are known. Rangefinders measure from a distance from the target subject and require that a line of sight to both the bottom and top of the object is present and that the elevation of the rangefinder is known.

By way of example, trees are commonly measured this way whereby a laser rangefinder is used to measure the straight line distances to the top and bottom of the tree and an inclinometer is used to measure the angles to the top and bottom of the tree. The heights of the tree above and below the level of the rangefinder are calculated and added to give the total height. This method suffers a number of drawbacks.

In particular, there are many sources of user error; the method is time consuming; and it requires the person conducting the measurement to be able to carry out trigonometric calculations. Furthermore, this method is unsuitable for accurately measuring the height of modestly sized subjects at close range, i.e. where space is limited. The accuracy of this method is also significantly affected if the laser rangefinder changes elevation between the two measurement stages. It is also almost impossible for a casual user to perform this measurement without introducing a change in elevation of one or more centimeter. Similarly, range finders are not appropriate for a single person to measure an animal as they measure from a distance, i.e. the animal cannot be kept still.

It is therefore an object of the present invention to provide a measuring device which mitigates the disadvantages of the prior art.

SUMMARY OF THE INVENTION

Accordingly, in one aspect of the present invention there is provided a height measuring apparatus adapted for placement upon the object to be measured, the apparatus comprising a main body portion and a movable portion, wherein the movable portion is movable relative to the main body portion and comprises a laser source and a photo detector.

The present invention advantageously provides a height measuring apparatus in which a laser beam can be directed at the ground in a non-perpendicular angle when the main body portion of the measuring apparatus is placed on the object to be measured. In this way, the laser beam can obtain a clear line of sight to the ground by avoiding the body being measured.

Advantageously therefore, the apparatus provides a means of taking a measurement of height directly from the object to be measured using a single point of reference, the point of reference being the ground which supports the object being measured.

In embodiments, the laser source and photo detector are located proximate, and in precise alignment with, each other.

Optionally, the laser source is provided with a lens and focus adjuster.

Optionally, photo detector is provided with a focus adjuster.

Optionally, the laser source and photo detector provide a laser rangefinder.

Optionally, the laser source is a laser diode.

Optionally, the main body portion and/or the movable portion comprises one or more of a circuit board or boards, batteries, a display and an on/off switch which activates the apparatus.

It will be appreciated that the circuit board, batteries, display and the on/off switch can each be located within the main body portion and/or the movable portion where appropriate.

Optionally, the on/off switch is provided on the main body portion and comprises a trigger mechanism. The trigger mechanism is depressed or activated when the main body portion is placed on the object to be measured. In this way, the trigger provides a signal which readies the height measuring apparatus for use.

Optionally, the trigger mechanism extends into a space defined by a recessed portion provided on the main body portion.

Optionally, the trigger mechanism comprises a capacitive touch switch.

In one embodiment, the main body portion and the movable portion are each provided with at least one tri-axial accelerometer.

In another embodiment, only the main body portion is provided with at least one tri-axial accelerometer.

Conveniently, the at least one tri-axial accelerometer associated with the main body portion is adapted to measure the angular orientation of said main body portion about its vertical, lateral and longitudinal axes.

Conveniently, the at least one tri-axial accelerometer associated with the movable portion is adapted to measure the angular orientation of said movable portion about its vertical, lateral and longitudinal axes.

Conveniently, the circuit board or boards support a processing means that is in communication with the laser source, photo detector and accelerometer(s).

In this way, the position of the laser and the photo detector with respect to the main body portion can be accurately determined with data values relating to spatial location and/or angular orientation being processable by the processing means in an overall height calculation.

In the embodiment where only the main body portion is provided with at least one tri-axial accelerometer, the orientation of the movable portion, and thus the of the laser/photodiode, with respect to the main body portion is fixable at one or more set reference points or orientations thus enabling a calculation of height to be made using data obtained via the at least one tri-axial accelerometer in the main body portion of the apparatus.

In embodiments, the vertical offset distance ("h") between the origin of the laser beam and the point of contact between the main body portion and the object to measured, is established.

In addition, in the embodiments, the provision of at least one inclinometer in the main body portion and/or the movable portion in communication with the processing means enables the angle of incidence ($\phi$) of the laser beam with the ground to be measured, and thus the and the laser path angle ($\theta$, theta) to be determined.

Conveniently, it has been found that when the laser beam is incident at the ground at a shallow angle, there is still sufficient beam reflected back along the path of incident laser beam for detection by the photo sensor. In this way a measurement of straight line beam distance (L) can be made.

Optionally, the measurement of straight line beam or 'laser path' distance (L) is determined using a measurement of the phase angle between the amplitude waveform of the transmitted laser beam and that of the reflected beam.

Conveniently, the processing means runs firmware programmed or adapted to convert the combination of laser path distance (measured by the photo detector in conjunction with the laser source) and laser path angle data determined by the tri-axial accelerometer(s), together with known constant dimensions of the apparatus, to obtain an accurate measurement of the height of the object being measured.

Preferably, the processing means is a microprocessor.

In one arrangement, the main body and movable portions are each constructed from respective shell halves which define housings which contain the necessary hardware, circuitry, processing means and power source for the measuring apparatus.

In one embodiment, the movable portion is slidably connected to the main body portion.

Optionally, at one end of the main body the respective shell halves are each formed having an outwardly curved side that terminates in an upstanding side wall.

Conveniently, the sidewalls are of a height such that when the shell haves are mated together, the terminal edges of the respective side walls are spaced apart so as to define an elongate slot.

Optionally, at one end of the movable portion each shell half is provided a corresponding inwardly curved side that terminates in a side wall having a projection extending outwardly therefrom.

Conveniently, the projection extending outwardly from the side wall of each shell half of the moveable portion defines a groove, each groove being adapted to receive a terminal edge of a side wall of the main body.

Advantageously, when the respective shell halves of the movable portion are mated together, the respective projections together define a substantially T-shaped member which engages in use with the elongate slot defined by the respective shell halves of the main body portion.

In this way, when the shell halves of the main body portion are mated together to form the completed measuring apparatus assembly, the movable portion is engaged with and slidable relative to the main body portion. In this way, the laser can be oriented at a range of different angles relative the main body portion so that the laser beam can be directed at whatever angle is necessary to avoid the body being measured and to obtain a clear line of sight to the ground.

In an alternative arrangement, the movable portion is pivotally connected to the main body portion.

Conveniently, the movable portion can be maintained (i.e. held in position) at a desired angle with respect to the main body portion.

Optionally, the moveable portion may be movable to one or more discrete incremental positions, each position corresponding to a specific pre-set angle of the movable portion with respect to the main body portion.

Optionally, the ne or more discrete incremental positions may be defined by one or more detents or other mechanical stops on the hinge associated with apparatus. In this way, the angular orientation of the movable portion about its lateral axis relative to that of the main body portion can be predetermined thereby obviating the need for an accelerometer in said movable portion. In this way, calculation of the height of the object to be measured can be made using data from a tri-axial accelerometer situated in the main body portion of the apparatus only.

It will be appreciated that the term 'tri-axial accelerometers' is not limited to discrete accelerometers measuring inclination in three axes, but also includes arrays or combinations of single axis or bi-axial accelerometers coupled to have the net function of a tri-axial accelerometer.

The invention further provides a method of obtaining a measurement of height of an object, the method comprising:
  placing a measuring apparatus upon the object to be measured;
  manually adjusting a movable portion of the measuring apparatus so that a laser source and photo detector on the movable portion establish a line of sight to the ground or other surface upon which the object to be measured is standing or is supported;
  activating the apparatus to send a frequency modulated laser beam from the laser source to the ground and automatically calculating the laser path distance (L) to the ground;
  automatically determining the angle of incidence of the laser beam $\phi$ with the ground and then calculating the laser path angle $\theta$;

automatically determining the vertical offset height (h) between the laser source and the point of contact of the main body portion with the object to be measured; and automatically calculating vertical height (H) of the object being measured; wherein the calculation for vertical height is performed by a processing means of the measuring apparatus.

Advantageously, the step of automatically determining the angle of incidence of the laser beam φ with the ground and then calculating the laser path angle θ includes automatically taking the outputs from one or more accelerometers provided in the apparatus, and determining any tilting of the apparatus about vertical and longitudinal axes of apparatus; and compensating for any tilt in the subsequent calculation of the laser path angle θ.

Desirably, the step of manually adjusting the movable portion of the measuring apparatus comprises slidably moving the movable portion relative to the main body portion.

Optionally, the step of manually adjusting the movable portion of the measuring apparatus comprises rotatably moving the movable portion relative to the main body portion.

The method further includes one or more of: displaying the calculated height on a display provided on the measuring apparatus; recording calculated height measurements; communicating height measurements to a remote server or servers; associating height measurement data with identifiers which relate to the object(s) being measured; adjusting the focus of the laser beam.

The preceding discussion of the background to the invention is intended only to facilitate an understanding of the present invention. It should be appreciated that the discussion is not an acknowledgement or admission that any of the material referred to was part of the common general knowledge as at the priority date of the application.

Throughout the description and claims of this specification, the words "comprise" and "contain" and variations of those words, for example "comprising" and "comprises", mean "including but not limited to", and are not intended to (and do not) exclude other components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

It will be understood that the word 'ground' as used throughout the claims and description should not be construed to mean the surface of the earth only, but rather describes any surface which supports the object being measured.

Features, integers or characteristics, and compounds described in conjunction with a particular aspect, embodiment or example of the invention are to be understood to be applicable to any other aspect, embodiment or example described herein unless incompatible therewith.

BRIEF DESCRIPTION OF THE DRAWINGS

The invention will now be described by way of non-limiting examples, with reference being made to the accompanying drawings, in which.

DESCRIPTION OF THE PREFERRED EMBODIMENTS

Figure 1A:
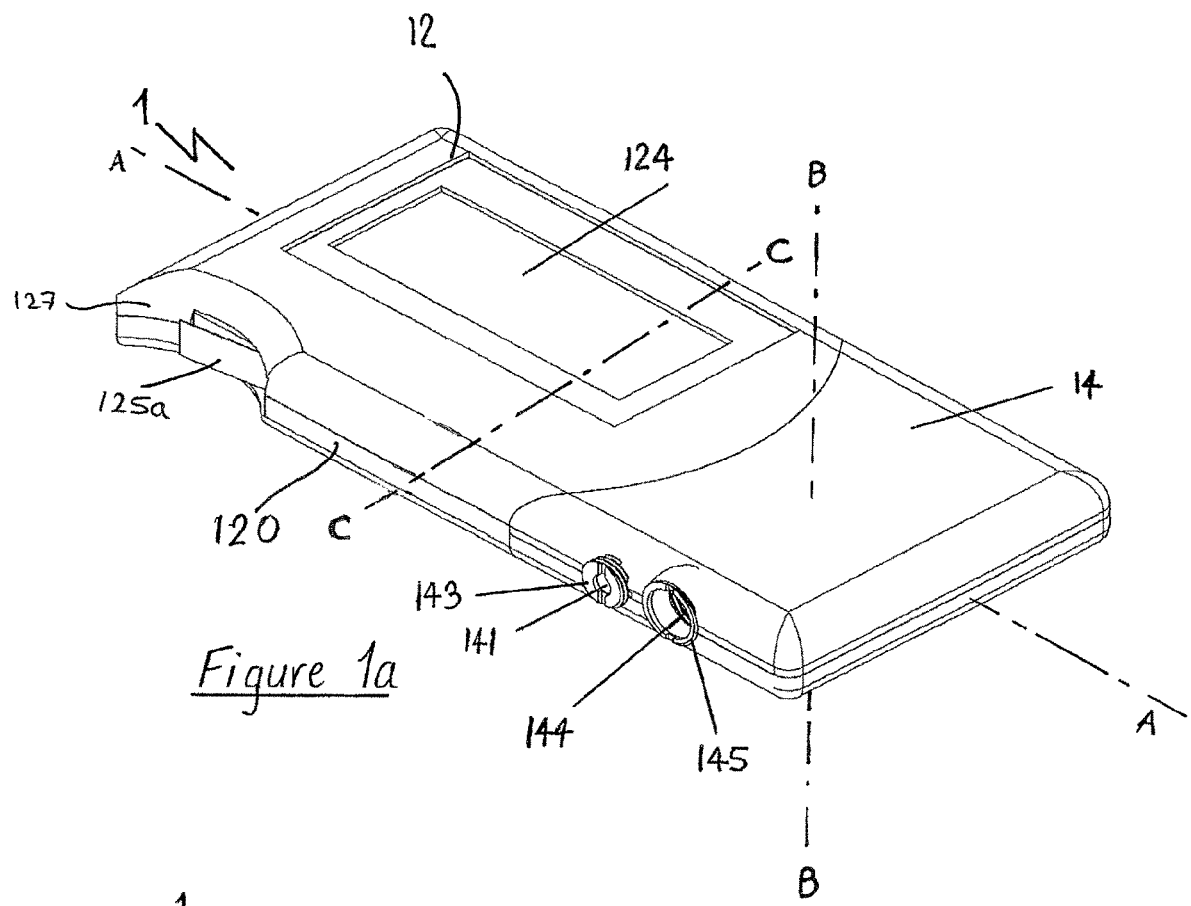
FIGS. 1a and 1b are schematic illustrations of an exemplary height measuring apparatus in accordance with the present invention and shown in opened and closed positions, respectively.

With reference to FIGS. 1a, 1b, 1c, 1d, 1e, 2a and 2b, there is shown embodiments of an exemplary measuring apparatus 1 in accordance with the present invention.

The measuring apparatus 1 provides a means to measure the height of an exemplary object 50 (FIG. 3) when placed on said object at a position from where the height measurement is to be taken. The measuring apparatus 1 comprises a main body portion 12 and a movable portion 14, wherein the movable portion 14 is movable relative to the main body portion and comprises a laser source 141 and a photo detector 144. The photo detector 144 preferably is a photo diode.

Measuring apparatus 1 is a slim, portable hand held device that can be stowed in a small space, for example a pocket of a garment or bag. Optionally, the apparatus has a thickness of 20 mm or less.

Figure 3:
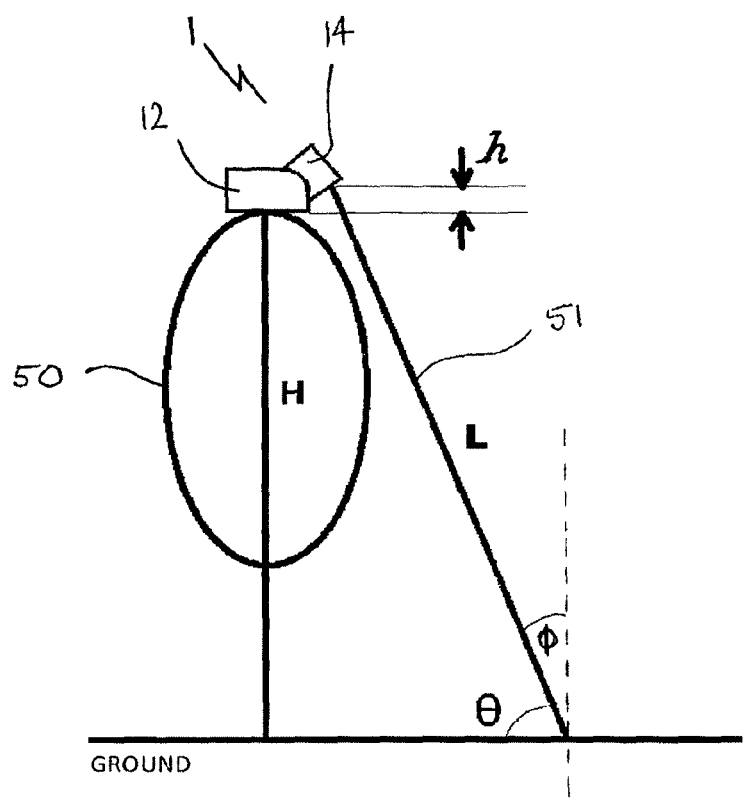
FIG. 3 is a schematic cross-sectional illustration showing the principle of operation of a height measuring apparatus in accordance with the present invention.

The size constraints imposed upon the measuring apparatus mean that it will not always span across, or project laterally from the point of contact with the object to be measured to an extent that a notional vertical (i.e. perpendicular) line of sight can be established with the ground surface below. Similarly, with certain objects the point of contact from which the height is to be measured may be obscured by other features of that object such that a notional vertical (i.e. perpendicular) line of sight cannot be established with the ground surface below. An example of such an exemplary subject 50 is shown in FIG. 3 where the body of the subject blocks a perpendicular view to the ground below, thereby preventing a substantially vertically directed laser beam from reaching the ground. However, with the present invention, it has been found that a derived measurement of vertical height can be made using a laser beam 51 (FIG. 3) that is incident at the ground at an angle that is substantially less than 90 degrees. The shape of the exemplary subject 50 shown in FIG. 1 is generally representative of a horse or other animal.

Figure 2A:
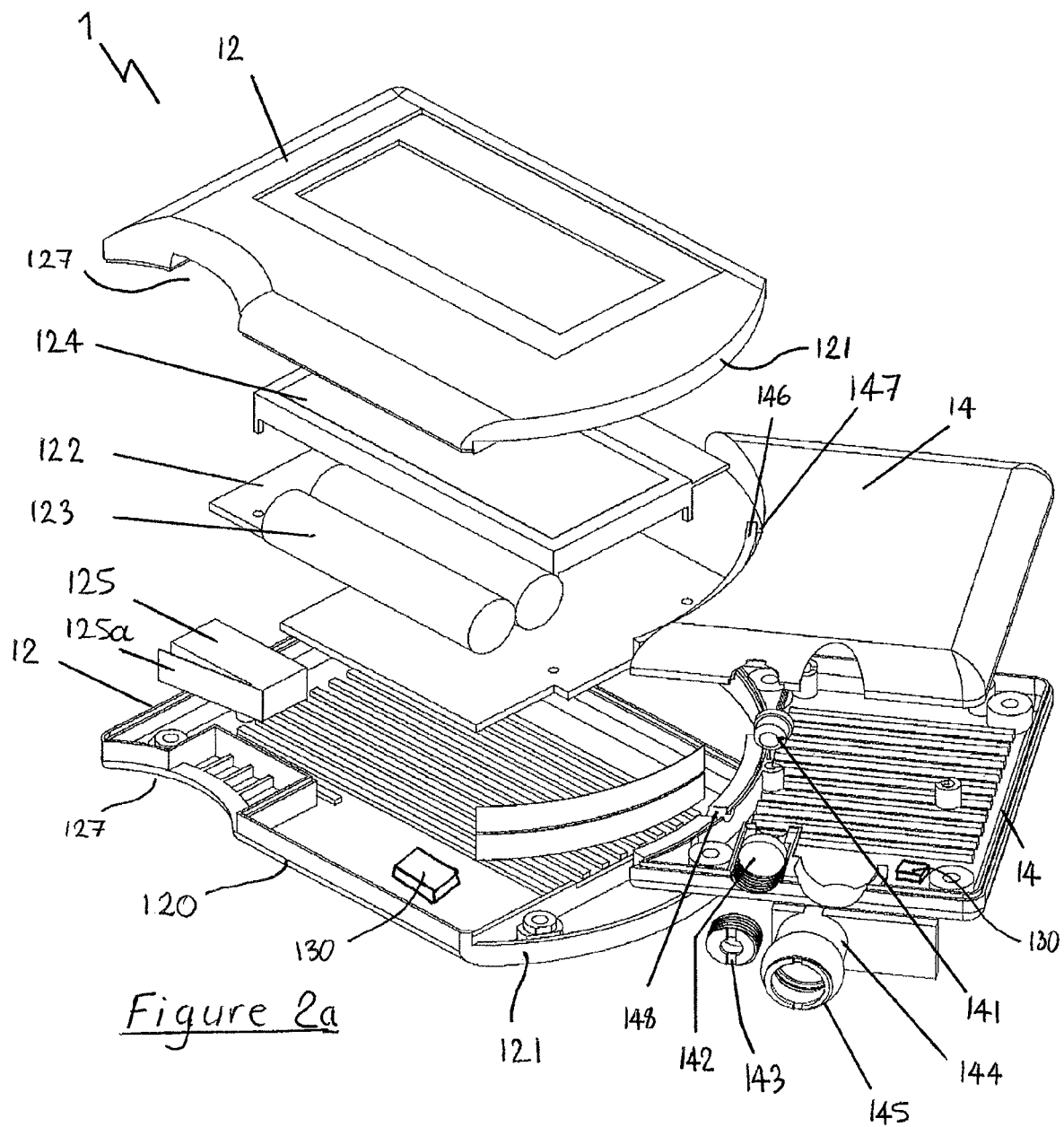
FIG. 2a is a detailed exploded schematic drawing of the exemplary height measuring apparatus of FIGS. 1a and 1b.
Figure 2B:
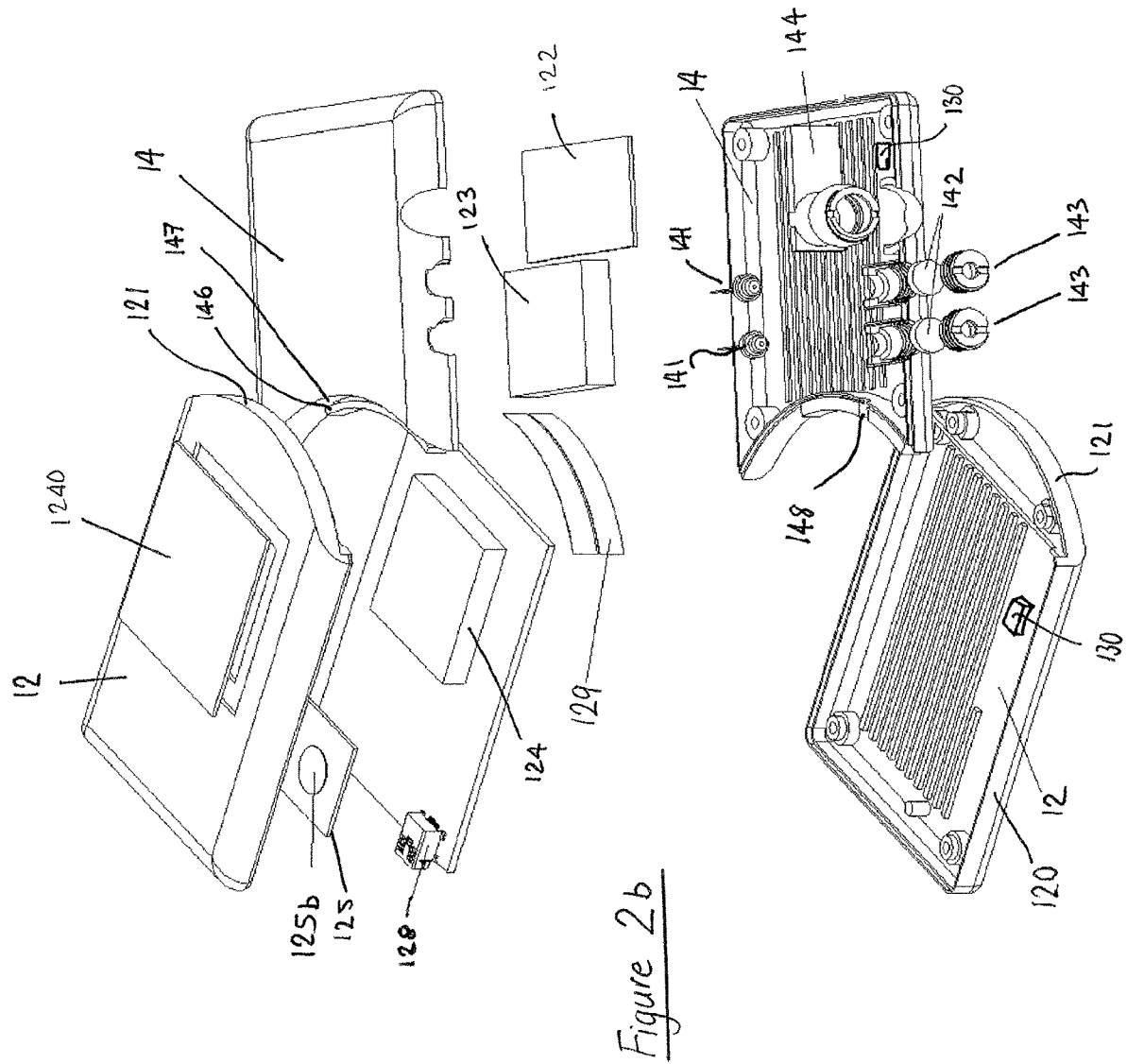
FIG. 2b is a detailed exploded schematic drawing of an exemplary height measuring apparatus.

With reference to FIGS. 2a and 2b, the main body 12 and movable 14 portions are each constructed from respective shell halves which define housings which house the necessary hardware, circuitry, processing means and power source for measuring apparatus 1.

As shown in the embodiment of FIG. 2a, the main body portion 12 comprises a circuit board 122, batteries 123, an LCD display 124 and an on/off switch 125 which activates the apparatus. The circuit board 122 supports a processing means (not shown) which runs firmware programmed or adapted to convert the combination of laser path distance (measured by the photo detector 144 in conjunction with the laser source 143 as described below) and laser path angle data, together with known constant dimensions of the apparatus, to obtain an accurate measurement of the height of the object being measured. Preferably, the processing means is a microprocessor. The height measurement is displayed on the LCD display 124 for immediate reading by a user.

It will be appreciated that the specific location of the respective circuitry, power supply and processing means is not limited to being in one or other of the main body 12 and movable portions 14. For example in the arrangement shown in FIG. 2b, the battery 123 and circuit board 122 are shown located within the movable portion 14.

Figure 1B:
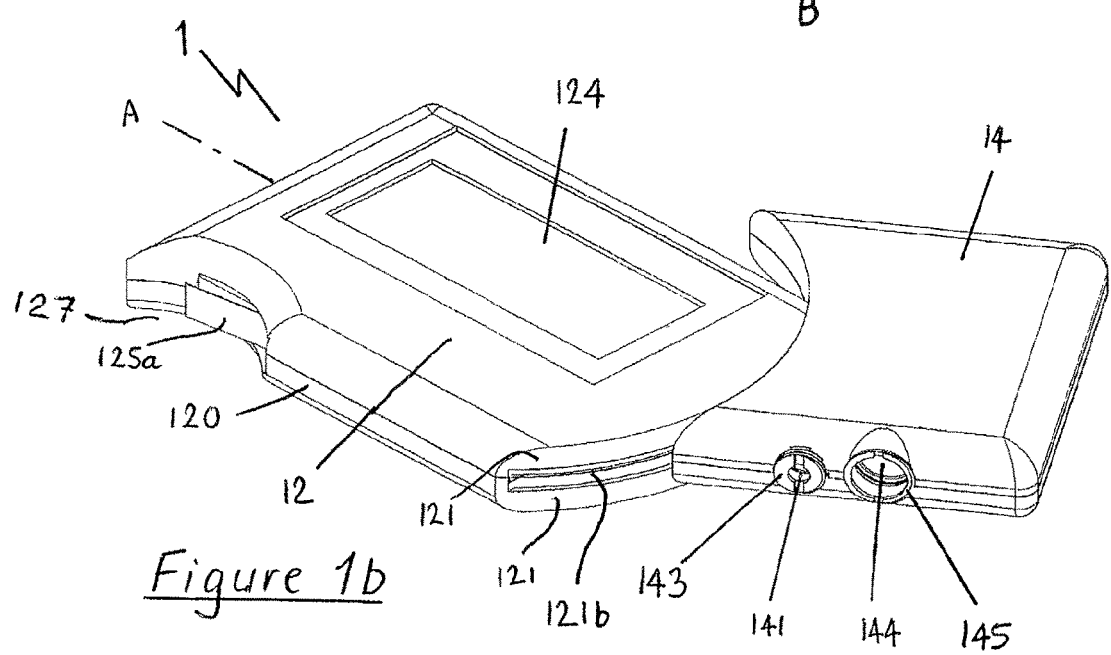

In the embodiment shown in FIGS. 1a, 1b and 2a, the on/off switch 125 is provided on the main body portion and comprises a trigger mechanism 125a. The trigger mechanism 125a can be depressed or activated when the main body portion is placed on the object to be measured. In this way, the trigger mechanism can provide a signal which readies the height measuring apparatus for use. In FIG. 2b a further transparent cover 124O is shown placed over display 124.

As shown in FIGS. 1a, 1b and 2a, the trigger mechanism 125a may be provided to extend into a space defined by a recessed portion 127 provided on an edge 120 of the main body portion 12. Such a recess 127 enables the measuring apparatus to engage positively with the withers an animal, for example a horse.

In an alternative arrangement as shown by way of example in FIG. 2b, the on/off switch comprises a capacitive touch switch 125b that is housed within the main body portion 12.

As shown by way of example in FIG. 2b, the measuring apparatus further comprises a socket 128, such as a USB connector, to enable external connection of the apparatus for the purposes or powering, battery recharging, data transfer and the likes.

Referring to FIGS. 1a, 1b and 2a, the movable portion comprises a laser source 141, such a laser diode, and a photo detector 144 (FIGS. 2a, 2b), the photo detector being located proximate to, and in precise alignment with, the laser source 141 and adapted to receive reflected laser light from said laser source. A lens 142 (FIG. 2) and focus adjuster 143 are also provided for control and adjustment of the beam of laser light emitted from the laser source 141. A focus adjuster 145 is provided in conjunction with the photo detector 144 in order to maximise the amount of reflected laser light that can be captured. The laser diode 141 and photo detector 144 together provide a laser range finder. Preferably, the laser source is a Class 2 laser.

In FIG. 2b, the movable portion is shown having two laser diodes 141, each with associated lens 142 and focus adjuster 143. In this way, one laser diode may be a primary IR laser for the purposes of height measurement and which is invisible to the human eye, while the other laser diode may be a visible laser to create a spot on the ground that is visible to the user of the apparatus. It will be appreciated that while the two laser diodes 141 of the arrangement in FIG. 2b are shown having their own respective lens and focus adjusters, it is possible that the a common lens may be shared. It will be appreciated however that a single, visible, laser (e.g. Class 2 laser) can be employed therefore obviating the requirement for a separate secondary laser diode to provide a visible spot.

In the embodiments as shown in FIGS. 1a, 1b, 2a and 2b and as described below, the movable portion 14 is slidably connected to the main body portion 12.

With reference to FIGS. 2a and 2b, at one end of the main body portion 12, the shell halves are each formed having an outwardly curved side that terminates in an upstanding side wall 121. The sidewalls are of a height such that when the shell haves are mated together, the terminal edges of the respective side walls 121 are spaced apart so as to define an elongate slot (121b, FIG. 1b). At one end of the movable portion 14 each shell half is provided a corresponding inwardly curved side that terminates in a side wall having a projection 146 extending outwardly therefrom, the projection defining a groove 147. Each groove 147 is adapted to receive a terminal edge of a side wall 121 of main body 14. When the respective shell halves of the movable portion 14 are mated together, the respective projections 146 together define a substantially T-shaped member which engages in use with the elongate slot 121b defined by the respective shell halves of the main body portion 12. Thus when the respective shell halves of the main body 12 and movable portion 14 are mated together to form the completed measuring apparatus assembly (as shown in FIGS. 1a, 1b), the movable portion 14 is engaged with and is slidable relative to the main body portion 12. In this way the connection of the movable portion to the main body portion is a sliding hinge. In this way, the laser 141 can be oriented at a range of different angles relative the main body portion 12 so that the laser beam can be directed at whatever angle is necessary or appropriate to avoid the body being measured and to obtain a clear line of sight to the ground. Conveniently, the geometry and/or dimensions of the substantially T-shaped member and the elongate slot 121b are such that they mutually frictionally engage in use, such that the movable portion 14 can dwell at any position to which it is moved with respect to the main body portion 12. Advantageously therefore, the movable portion 14 can be maintained (i.e. held in position) at any desired angle with respect to the longitudinal axis A-A (FIG. 1) of the apparatus.

It will be appreciated that the outwardly curved sides do not necessarily have to comprise the terminal ends of the main body portion as shown in FIGS. 1a, 1b, by rather may be hidden from view inboard of the terminal ends of the main body portion.

It will be appreciated that the movable portion 14 is movable relative to the main body portion 12 such that the laser 141 and photo diode 144 may be oriented an any angle between 0°-89° relative to the longitudinal axis A-A (FIG. 1) of the measuring apparatus to provide a height measurement. For example, in FIG. 1 the movable portion 14 is substantially in alignment with the main body portion 12 (i.e. the hinge is at a "closed" or 0° position). In this orientation, whereby the 141 and photo diode 144 are aligned substantially perpendicular to the longitudinal axis A-A of the measuring apparatus, a height measurement can be made by placing part or all of the movable portion 14 of measuring apparatus outwardly over an edge of the object to be measured.

Figure 1C:
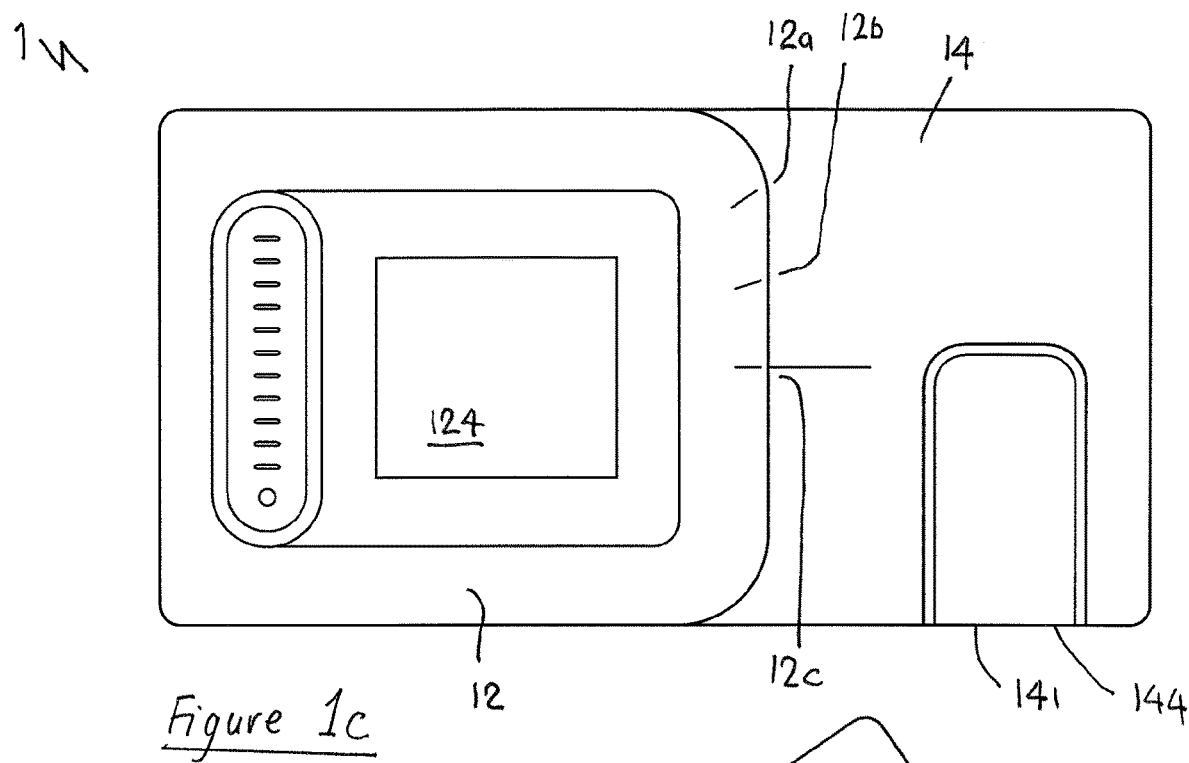
FIGS. 1c and 1d are schematic illustrations of an exemplary height measuring apparatus in accordance with the present invention and shown in opened and closed positions, respectively.
Figure 1D:
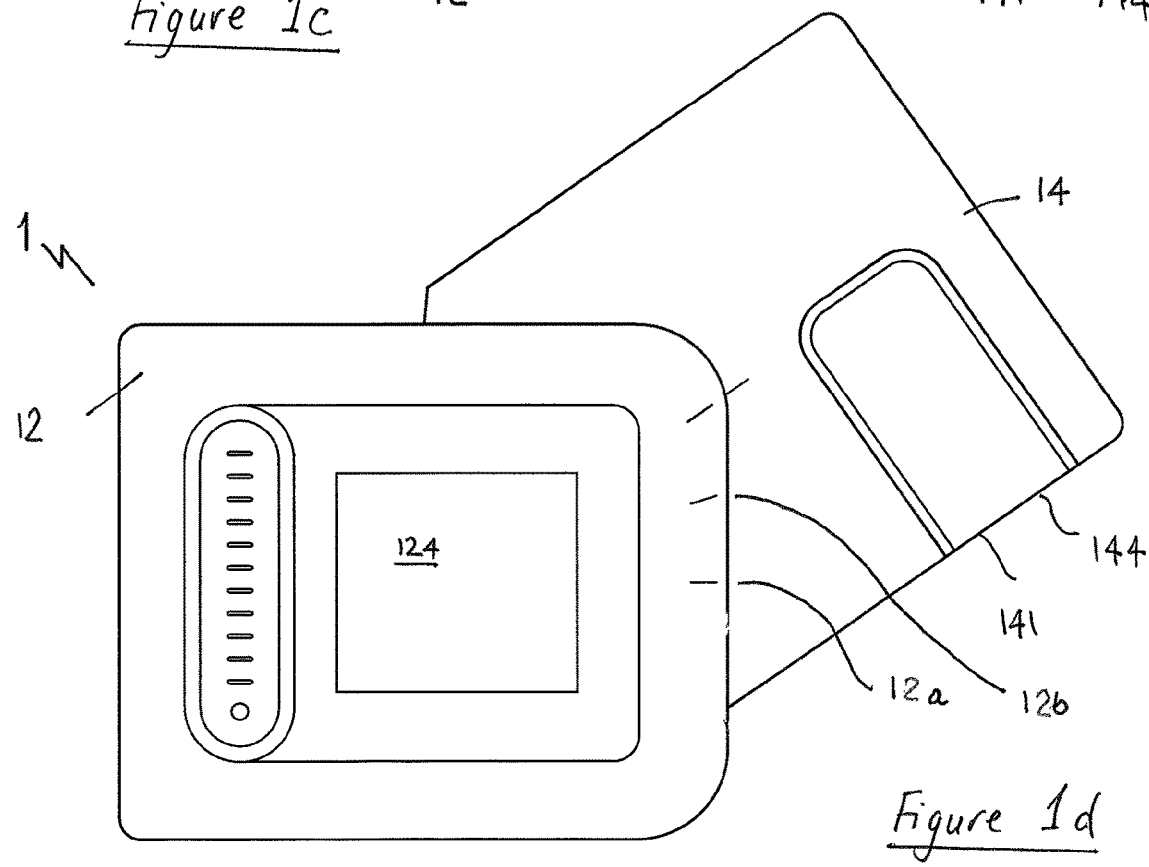

In one arrangement as shown by way of example in FIGS. 1c and 1d, the moveable portion 14 may be movable to one or more discrete incremental positions with respect to the main body portion 12. These positions are shown by way of example as 12a, 12b, 12c, each position corresponding to a specific pre-set angle of the movable portion with respect to the main body portion. Such positions may be defined by one or more detents or other mechanical stops on the hinge means associated with apparatus. In this way, the angular orientation of the movable portion 14 about the lateral axis B-B of the apparatus can be set at one or more pre-set angles, thereby obviating the need for an accelerometer in said movable portion to measure the angle of said movable portion with respect to the longitudinal axis A-A of the apparatus. This is because the distance between the laser path axis and the main body portion will be a known constant value based on the or each discrete incremental position, thereby enabling height "h" to be calculated using the angular orientation of the laser path axis. In this way, calculation of the height of the object to be measured can be made using data from a tri-axial accelerometer situated in the main body portion of the apparatus only.

As shown in FIGS. 2a and 2b, a dust cover 129 is provided between the main body portion 12 and the movable portion 14.

Figure 1E:
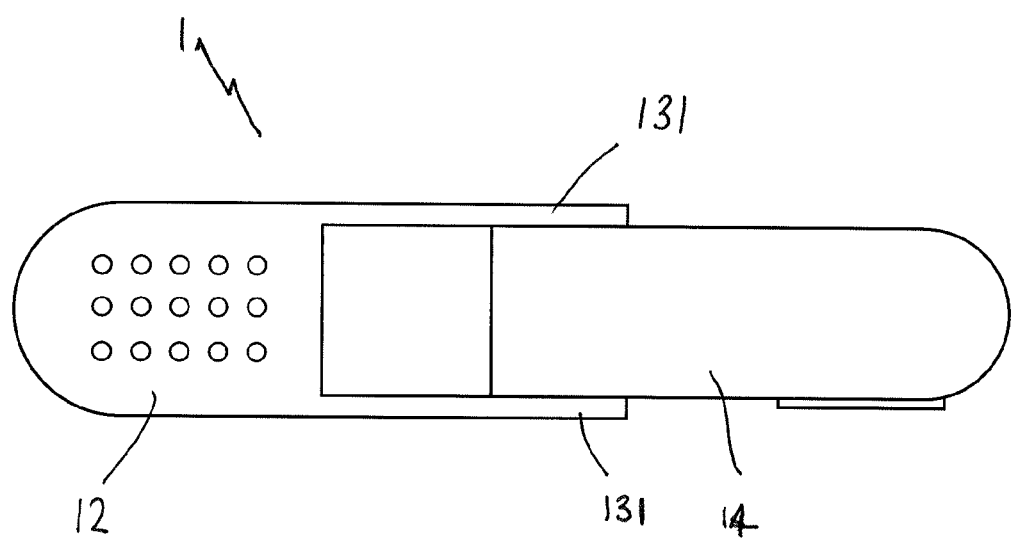
FIG. 1e is a schematic plan view of an exemplary height measuring apparatus in accordance with the present invention.

It will be appreciated that the movable portion 14 may alternatively be arranged to be pivotally movable with respect to the main body portion 12. For example, the movable portion 14 may be connected to the main body portion 12 by means of a hinge. Similarly, the movable portion may be rotatable with respect to the main body portion 12. FIG. 1e shows by way of example how the main body portion 12 may be provided with spaced apart flanges 131 between which the movable portion is pivotally mounted.

Conveniently, a port 148 provided in movable portion 14 allows for electrical connection of the powered components of said movable portion 14 with the hardware, circuitry, processing means and power source housed within the main body portion 12.

It has been found that even when the laser beam 51 is incident at the ground surface which supports the object being measured a shallow angle there is still sufficient beam reflected back along the path of incident laser beam for detection by the photo detector 144. Thus a measurement of straight line beam distance can be made (as indicated by distance "L" in FIG. 3).

The measurement of distance L is determined by modulating the laser light is amplitude modulated with a high frequency wave (10-20 MHz) and then comparing this modulating waveform with the corresponding waveform obtained from the reflected signal as detected by the photo detector 144 adjacent to the source 141 of the laser beam. The beam reflected from the ground will manifest a phase delay compared with the modulating signal as a consequence of the time of flight incurred by the distance travelled by the laser beam along the return journey from the laser beam source to the ground and back. Accordingly, the phase angle or delay between the amplitude waveform of the transmitted beam 51 and that of the reflected beam is a direct function of the time of flight. Thus measurement of the phase angle indicates the time of flight. As the speed of light is a constant, and as the time of flight is known from the phase angle, the length of the beam path, i.e. distance L, can be calculated. This phase delay is extracted using a conventional heterodyne circuit within the measuring apparatus whereby the high frequency signals are mixed with a common local oscillator signal to obtain two resulting signals that have much lower frequency but the same phase angle as the original pair of signals (modulating and reflected). At this lower frequency this phase angle is determined by a simple microprocessor timer circuit incorporated within the measuring apparatus and/or in communication with the processing means.

In normal circumstances, the fraction of laser light that is reflected back along the beam path (51, FIG. 3) is so small it would ordinarily be discarded as worthless and is therefore ignored. However, with the present invention it has been found that the loss in reflected laser light is tolerable such that an accurate distance measurement can be made using the apparatus of the present invention.

By way of example, as described above, main body portion 12 and the movable portion 14 may each be provided with a tri-axial accelerometer 130. The tri-axial accelerometer associated with the main body portion 12 is adapted to measure the angular orientation of said main body portion 12 about the vertical (C-C), lateral (B-B) and longitudinal (A-A) in use axes of the apparatus. The tri-axial accelerometer associated with the movable portion 14 is adapted to measure the angular orientation of said movable portion about its vertical, lateral and longitudinal axes. The respective tri-axial accelerometers 130 are in communication with the processing means. Thus, the position of the laser 141 and the photo detector 144 with respect to the main body portion 12 can be accurately determined and the data values relating to spatial location being usable by the processing means in an overall height calculation. In particular, the distance "h" (see FIG. 3), which is the vertical offset distance between the origin of the laser beam and the point of contact between the main body portion 12 and the object to measured, is established. In addition, the provision of tri-axial inclinometers in the main body portion 12 and/or the movable portion 14 which are in communication with a processing means enables the angle of incidence φ of the laser to the ground to be automatically measured and the laser path angle θ (theta) to be determined, taking into account any tilt of the apparatus about its axes from the precise horizontal and vertical planes.

The use of tri-axial accelerometers in both the main body portion 12 and the movable portion 14, or the use of a tri-axial accelerometer in just the main body portion in conjunction with the movable portion being movable to one or more discrete incremental positions with respect to the main body portion 12, means that a user is not required to be meticulous in placing the measuring apparatus 1 in a horizontal orientation on the object to be measured. This is because the tri-axial accelerometer(s) and associated processing means can automatically compensate for apparatus orientation in use and relative hinge angle in order to correctly determine the true angle of the laser beam. In addition, they can also determine and make correction for any minor vertical offset of the source 141 of the laser beam 51 arising from inclination of the measuring apparatus from an optimum horizontal orientation.

As described above, the processing means, optionally a microprocessor, runs firmware programmed or adapted to convert the combination of laser path distance L, offset height h and laser path angle data θ, together with known constant dimensions of the apparatus to obtain an accurate measurement of the vertical height H of the object being measured. The calculation for vertical height is performed by the processing means based on established trigonometric formulae, for example the formula $$H = L\sin(\theta) - h$$

The resultant height measurement is displayed on the LCD 124 for immediate reading by a user. Conveniently, the calculated vertical height can be displayed in appropriate units selected by the user and chosen from a menu stored on the processing means.

With reference to FIG. 2b, an example of a mode of use of the apparatus comprises the following steps:

a) holding the apparatus by gripping the main body portion 12;

b) tapping and holding the area on the main body portion 12 which is proximate the capacitive touch switch 125b to activate the apparatus;

c) after a delay of approximately two seconds the display 124 activates and pressure on the capacitive touch switch 125*b* can be released;

d) placing an edge 120 of the main body portion 120 of the apparatus onto an upper surface of the object to be measured, the apparatus being held in an approximately level orientation;

e) tapping the main body portion 12 proximate the capacitive touch switch 125*b* to activate measurement mode;

f) adjusting the movable portion 14 so that the laser establishes a line of sight to the ground;

g) tapping the main body portion 12 proximate the capacitive touch switch 125*b* in order to freeze the displayed height measurement;

h) if necessary, tapping main body portion 12 proximate the capacitive touch switch 125*b* again to reactivate measurement mode;

i) tapping and holding the main body portion 12 proximate the capacitive touch switch 125*b* to turn off the apparatus; or alternatively k) leaving the apparatus for approximately 30 seconds for automatic switch off.

As the operation of the measuring apparatus is instantaneous and silent, it is particularly suited for use in the measurement of horses. This is because horses generally do not stand still for sufficiently long periods to make accurate measurements using traditional techniques and because they are easily unsettled by unfamiliar noises in close proximity. It will be appreciated, however, that a height measuring apparatus in accordance with the present invention is not limited to use with animals, but rather is suitable for use with anything which the apparatus can be placed in contact.

Conveniently, the measuring apparatus optionally includes the following beneficial features:

Date and time stamping of measurements made

Photo, video and/or audio recording means

Scanning and reading RFID or other chip-based technologies

Wireless communication with remote server

Interfacing with "smart" devices and applications ("apps") running on said devices Means to sense vital signs and/or take appropriate biometric measurements Ability to receive or upload pre-prepared data sets (e.g. lists of people, patients, animals etc.)

The ability to measure other physical dimensions and parameters of physical space.

While the embodiments of the invention have been described as being slim and pocket-sized, it would be understood that the size of the measuring apparatus is not limited. For example, where heights to be measured are substantially greater than that of a human or animal, more powerful laser diodes, photo detectors and batteries etc. may be required and so the apparatus may require accordingly increased dimensions. In other words, it will be appreciated that height measuring apparatuses in accordance with the present invention may be particularly optimized for measurement of specific height ranges that are appropriate to particular groups of subjects that are most commonly measured by specific user groups.

It will be understood from the foregoing description that the apparatus in accordance with the invention provides a number of distinct advantages, which include the ability to use a laser beam that can be inclined at an angle from the horizontal and shone at the ground with no aiming mechanism and no requirement to aim at any particular reference point or target on the ground. In this way the need for accurate aiming mechanisms, eye pieces, tripods and specific specialised training etc. is obviated. Furthermore, through the provision of a movable portion, the angle of the laser beam can be configured at an optimum angle to suit a shoulder of an object being measured. Still furthermore, the use of a plurality of tri-axial accelerometers provides automatic compensation for any angle of apparatus orientation in use and thereby obviates any requirement for a user to be exact in how the apparatus is placed on the object being measured. Thus minimum user skill is required.

The invention claimed is:

1. A height measuring apparatus comprising a main body portion adapted for placement upon an object to be measured, and a movable portion which is movable relative to the main body portion, wherein the movable portion comprises a laser source and a photo detector, the movable portion being movable so that a laser beam from the laser source can be directed to the ground when the main body is placed on the object to be measured, and wherein the main body portion is provided with at least one tri-axial accelerometer being configured to measure the angular orientation of the main body portion, wherein the movable portion is connected by a hinge to the main body portion and wherein the movable portion and the main body portion are each constructed from respective shell halves, which define housings that house the laser source, the photo detector, the tri-axial accelerometer(s), the processor, a battery power source, a display and an on/off switch of the height measuring apparatus and wherein the shell halves of the main body portion are each formed having an outwardly curved side that terminates in an upstanding side wall, wherein the sidewalls are of a height such that when the main body portion shell haves are mated together, the terminal edges of the respective side walls are spaced apart so as to define an elongate slot.

2. A height measuring apparatus as claimed in claim 1, wherein the movable portion is provided with at least one tri-axial accelerometer, the tri-axial accelerometer being configured to measure the angular orientation of the movable portions with respect to the main body portion.

3. A height measuring apparatus as claimed in claim 1, wherein the laser source, the photo detector and the tri-axial accelerometer(s) are in communication with a processor, the processor being configured to determine the angle of incidence of the laser beam to the ground, and to determine the vertical offset distance between the laser source and the point of contact of the main body portion with the object being measured.

4. A height measuring apparatus as claimed in claim 3, wherein the laser beam is frequency modulated, and wherein the processor is configured to measure the phase angle or phase delay between the amplitude waveform of laser beam transmitted from the laser source and that of the reflected beam from the ground to the photo detector.

5. A height measuring apparatus as claimed in claim 4, wherein the processor runs firmware programmed or adapted to convert a combination of the phase angle or phase delay, the angle of incidence of the laser beam to the ground, and the vertical offset distance between the laser source and the point of contact of the main body portion with the object being measured, into a measurement of the height of the object being measured.

6. A height measuring apparatus as claimed in claim 1, wherein the movable portion and the elongate slot of the main body portion is in a frictional sliding engagement so that the laser source and the photo detector on the movable portion can be oriented and maintained at an angle between 0°-89° relative to a longitudinal axis of the main body portion.

7. A height measuring apparatus as claimed in claim 1, wherein the moveable portion is movable to one or more discrete incremental positions with respect to the main body portion.

8. A height measuring apparatus as claimed in claim 1, wherein the laser source is a laser diode and the photo detector is a photo diode.

9. A height measuring apparatus as claimed in claim 8, wherein each of the laser diode and photo diode are provided with a focus adjuster.

10. A height measuring apparatus as claimed in claim 1, wherein the apparatus further comprises photo, and/or video and/or audio recording means.

11. A height measuring apparatus as claimed in claim 1, wherein the apparatus further comprises an RFID reader.

12. A height measuring apparatus as claimed in claim 1, wherein the apparatus further comprises wireless communication means.

\* \* \* \* \*